United States Patent
Annis et al.

(10) Patent No.: US 7,732,357 B2
(45) Date of Patent: Jun. 8, 2010

(54) DISPOSABLE NONWOVEN WIPING FABRIC AND METHOD OF PRODUCTION

(75) Inventors: Vaughan R Annis, South Windsor, CT (US); Margaret Anne McDade, Eyemouth (GB)

(73) Assignee: Ahlstrom Nonwovens LLC, Windsor Locks, CT (US)

( * ) Notice: Subject to any disclaimer, the term of this patent is extended or adjusted under 35 U.S.C. 154(b) by 0 days.

(21) Appl. No.: 10/380,644

(22) PCT Filed: Sep. 14, 2001

(86) PCT No.: PCT/US01/28620

§ 371 (c)(1),
(2), (4) Date: Mar. 14, 2003

(87) PCT Pub. No.: WO02/22352

PCT Pub. Date: Mar. 21, 2002

(65) Prior Publication Data

US 2004/0013859 A1    Jan. 22, 2004

Related U.S. Application Data

(60) Provisional application No. 60/233,086, filed on Sep. 15, 2000.

(51) Int. Cl.
D04H 1/00 (2006.01)
(52) U.S. Cl. .................. 442/364; 442/408; 442/409; 442/411; 28/104
(58) Field of Classification Search .......... 442/408, 442/364, 409, 411; 28/104
See application file for complete search history.

(56) References Cited

U.S. PATENT DOCUMENTS

| | | | |
|---|---|---|---|
| 3,563,241 A | 2/1971 | Evans et al. | 128/284 |
| 3,881,210 A | 5/1975 | Drach et al. | 15/104.93 |
| 3,939,836 A | 2/1976 | Tunc | 128/284 |
| 4,002,171 A | 1/1977 | Taft | 128/284 |
| 4,117,187 A | 9/1978 | Adams et al. | 428/286 |
| 4,309,469 A | 1/1982 | Varona | 428/74 |
| 4,319,956 A | 3/1982 | Snyder et al. | |
| 4,362,781 A | 12/1982 | Anderson | 428/291 |
| 4,419,403 A | 12/1983 | Varona | 428/288 |
| 4,537,807 A | 8/1985 | Chan et al. | 428/74 |
| 4,548,856 A | 10/1985 | Ali Khan et al. | |

(Continued)

FOREIGN PATENT DOCUMENTS

| | | |
|---|---|---|
| EP | 0106604 | 4/1984 |
| EP | 0171806 | 2/1986 |
| EP | 0538047 | 4/1993 |
| EP | 0624676 | 11/1994 |

(Continued)

OTHER PUBLICATIONS

"Crystallization and Melting Behavior of Polyethylene Oxide Copolymers" vol. 35, Number, Jan. 1964, Simon et al.*

(Continued)

*Primary Examiner*—Elizabeth M Cole
(74) *Attorney, Agent, or Firm*—Alix, Yale & Ristas, LLP

(57) ABSTRACT

Disclosed is a fibrous nonwoven web material and a method of manufacture thereof. The fibrous nonwoven web material includes natural cellulose fibers, manmade cellulose fibers and synthetic fibers. The manmade cellulose fibers are preferably high crystallinity cellulose fibers. The fibrous nonwoven web material has appreciable wet strength yet is capable of dispersing in most aqueous environments with only mild agitation. The fibrous nonwoven web material can be wet laid from an aqueous dispersion of fibers.

21 Claims, 2 Drawing Sheets

U.S. PATENT DOCUMENTS

| | | | |
|---|---|---|---|
| 4,551,378 | A | 11/1985 | Carey, Jr. |
| 4,749,423 | A | 6/1988 | Vaalburg et al. |
| 4,755,421 | A | 7/1988 | Manning et al. ............ 428/224 |
| 4,874,666 | A | 10/1989 | Kubo et al. |
| 4,883,707 | A | 11/1989 | Newkirk |
| 4,963,230 | A | 10/1990 | Kawase et al. |
| 4,981,749 | A | 1/1991 | Kubo et al. |
| 5,033,172 | A | 7/1991 | Harrington |
| 5,045,387 | A | 9/1991 | Schmalz |
| 5,082,720 | A | 1/1992 | Hayes |
| 5,108,820 | A | 4/1992 | Kaneko et al. |
| 5,167,765 | A | 12/1992 | Nielsen et al. |
| 5,173,154 | A | 12/1992 | Heinrich |
| 5,192,606 | A | 3/1993 | Proxmire et al. |
| 5,227,107 | A | 7/1993 | Dickenson et al. |
| 5,246,772 | A | 9/1993 | Manning |
| 5,256,417 | A | 10/1993 | Koltisko ..................... 424/402 |
| 5,264,269 | A | 11/1993 | Kakiuchi et al. ............ 428/156 |
| 5,269,994 | A | 12/1993 | Deffenbaugh et al. |
| 5,288,348 | A | 2/1994 | Modrak |
| 5,292,581 | A * | 3/1994 | Viazmensky et al. ........ 442/408 |
| 5,328,759 | A | 7/1994 | McCormack et al. |
| 5,382,400 | A | 1/1995 | Pike et al. |
| 5,391,161 | A * | 2/1995 | Hellgren et al. ............. 604/366 |
| 5,409,768 | A | 4/1995 | Dickenson et al. |
| 5,431,994 | A | 7/1995 | Kozulla |
| 5,470,640 | A | 11/1995 | Modrak |
| 5,498,463 | A | 3/1996 | McDowall et al. |
| 5,500,068 | A | 3/1996 | Srinivasan et al. .......... 156/148 |
| 5,500,281 | A | 3/1996 | Srinivasan et al. .......... 428/288 |
| 5,509,913 | A | 4/1996 | Yeo ............................ 604/364 |
| 5,540,992 | A | 7/1996 | Marcher et al. |
| 5,573,841 | A | 11/1996 | Adam et al. |
| 5,582,667 | A | 12/1996 | Gupta et al. |
| 5,605,739 | A | 2/1997 | Stokes et al. |
| 5,643,240 | A | 7/1997 | Jackson et al. |
| 5,667,635 | A | 9/1997 | Win et al. ................... 162/109 |
| 5,669,798 | A | 9/1997 | Koczab |
| 5,780,155 | A | 7/1998 | Ishizawa et al. |
| 5,783,505 | A * | 7/1998 | Duckett et al. .............. 442/411 |
| 5,885,390 | A | 3/1999 | Alkire et al. |
| 5,905,046 | A * | 5/1999 | Takeda et al. ............... 442/416 |
| 5,914,177 | A | 6/1999 | Smith, III et al. ........... 428/195 |
| 5,916,678 | A | 6/1999 | Jackson et al. .............. 428/373 |
| 5,935,880 | A * | 8/1999 | Wang et al. .................. 442/65 |
| 5,945,480 | A | 8/1999 | Wang et al. .................. 525/58 |
| 5,948,710 | A | 9/1999 | Pomplun et al. ............ 442/341 |
| 5,952,251 | A | 9/1999 | Jackson et al. ............. 442/340 |
| 5,976,694 | A * | 11/1999 | Tsai et al. ................... 428/373 |
| 5,981,410 | A * | 11/1999 | Hansen et al. .............. 442/361 |
| 6,645,622 | B2 * | 11/2003 | Yamane ....................... 428/364 |
| 2003/0104204 | A1 * | 6/2003 | Bond et al. .................. 428/373 |

FOREIGN PATENT DOCUMENTS

| | | |
|---|---|---|
| EP | 671496 A1 * | 9/1995 |
| EP | 0685586 | 12/1995 |
| EP | 000964093 A1 * | 12/1999 |
| GB | 904826 | 11/1960 |
| JP | 01-298276 | 12/1989 |
| JP | 02-234946 | 9/1990 |
| JP | 03-193929 | 8/1991 |
| JP | 03-213553 | 9/1991 |
| JP | 03-213554 | 9/1991 |
| JP | 03-213555 | 9/1991 |
| JP | 03-294558 | 12/1991 |
| JP | 04-065537 | 3/1992 |
| JP | 04-065543 | 3/1992 |
| JP | 04-163339 | 6/1992 |
| JP | 04-245907 | 9/1992 |
| JP | 5025764 | 2/1993 |
| JP | 05-059616 | 3/1993 |
| JP | 05-186946 | 7/1993 |
| JP | 05-186954 | 7/1993 |
| JP | 5179548 | 7/1993 |
| JP | 06-002211 | 1/1994 |
| JP | 6-65851 | 3/1994 |
| JP | 6101154 | 4/1994 |
| JP | 06-235115 | 8/1994 |
| JP | 06-264309 | 9/1994 |
| JP | 06-315407 | 11/1994 |
| JP | 7070896 | 3/1995 |
| JP | 08-035156 | 2/1996 |
| JP | 08-060440 | 3/1996 |
| JP | 08-060442 | 3/1996 |
| JP | 08-323070 | 12/1996 |
| JP | 09-013281 | 1/1997 |
| JP | 09-059860 | 3/1997 |
| JP | 10183471 | 7/1998 |
| JP | 10310960 | 11/1998 |
| JP | 11012909 | 1/1999 |
| JP | 11043854 | 2/1999 |
| JP | 11047026 | 2/1999 |
| JP | 11047027 | 2/1999 |
| JP | 11093055 | 4/1999 |
| JP | 11152667 | 6/1999 |
| JP | 11200296 | 7/1999 |
| WO | WO 95/05101 | 2/1995 |
| WO | WO 96/30576 | 10/1996 |
| WO | WO 97/18346 | 5/1997 |
| WO | WO 98/48684 | 11/1998 |
| WO | WO 0148281 A2 * | 7/2001 |

OTHER PUBLICATIONS

International Search Report, International Application No. PCT/US01/28620, International Filing Date Sep. 14, 2001; 2 pages.

* cited by examiner

DISPOSABLE NONWOVEN WIPING FABRIC AND METHOD OF PRODUCTION

The present application is the U.S. National Phase of PCT International Application No. PCT/US01/28620 having an International Filing Date of Sep. 14, 2001 which claims the benefit of U.S. Provisional Patent Application No. 60/233,086 filed Sep. 15, 2000.

BACKGROUND OF THE INVENTION

The present invention relates generally to a new and improved fibrous nonwoven sheet material having sufficient wet strength to be used as a premoistened wipe. In some embodiments, the inventive sheet material is also capable of disintegrating into small pieces and individual fibers with mild agitation in moving water after a brief period of time and disposal in a sanitary waste system.

Nonwoven sheet material is commonly cut into individual wiping sheets. While the cut sheets may be used dry, more typically the individual sheets are saturated with a chemical solution suited for an intended end use, stacked and wrapped in a liquid tight package for subsequent dispensing. The chemical solution often includes bactericides and other biological control agents as well as emulsifiers, pH buffers, perfumes and the like. The liquid tight packaging maintains the saturated condition of the wiping sheet until use.

Such premoistened wiping sheets, also called wet wipes or simply, wipes, are commonly used by consumers for cleaning or wiping, particularly when wash water is not readily available or cannot be conveniently used. Travelers and parents of small children find such wipes especially convenient. These wipes are also useful for applying or removing makeup, cleansing parts of the body, as a substitute for conventional dry toilet paper and for household cleaning. A high wet tensile strength to resist tearing or puncturing of the premoistened wipe during dispensing and use is very desirable.

As will be appreciated, it is often desirable to dispose of used premoistened wipes through a sewer or septic system. Thus, while premoistened wipes must have sufficient wet strength to resist tearing and puncturing during vigorous use, they also must easily and readily break up into smaller pieces and fibers within the moving water present in a sanitary or septic system and preferably be substantially totally biodegradable.

Premoistened wipes or sheet material capable of breaking up within a septic system are known. Some wipes described heretofore have utilized a pH sensitive water-soluble binder or adhesive to achieve the requisite wet strength during packaging and use. The binders of such wipes exhibit a resistance to weakening during storage in a controlled pH solution, but are much more loosely bonded when the wipe has been immersed in a relatively large amount of turbulent, substantially neutral water. One such wet wipe is described in U.S. Pat. No. 4,117,187 to Adams et al. Such wipes typically work within a chemical solution having a limited pH range and are difficult to break up in other than the preferred, substantially neutral pH, environment.

Other sheet materials completely eliminate any binder system. These wipes rely solely on hydroentanglement of the fibers comprising the sheet material to achieve the strength required for processing and for one time use. Such sheet materials disentangle when exposed to agitation so that they can be disposed of in sewer and septic systems. A material of this type is described in U.S. Pat. No. 4,755,421 to Manning et al, the disclosure of which is incorporated herein by reference. That patent describes a binder free, hydroentangled web material consisting essentially of a blend of rayon fibers and papermaking pulp. While such materials exhibit acceptable absorption characteristics, the wet strength of such materials, particularly at low basis weights, has proven to be relatively poor. In fact, the present inventors have been unable to duplicate the results of Manning at basis weights below 55 grams per square meter.

Definitions

Bicomponent fibers—Fibers that have been formed from at least two polymers extruded from separate extruders through a single spinneret hole to form a single filament. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another or a side by side arrangement.

Cellulose fibers—Natural, e.g. non-manmade, cellulosic fibers from natural sources such as woody and non-woody plants. Woody plants include, for example, deciduous and coniferous trees. Non-woody plants include, for example, cotton, flax, esparto grass, sisal, abaca, milkweed, straw, jute, hemp, and bagasse.

Cross machine direction (CD)—The direction perpendicular to the machine direction.

Denier—A unit used to indicate the fineness of a filament given by the weight in grams for 9,000 meters of filament. A filament of 1 denier has a mass of 1 gram for 9,000 meters of length.

Lyocell—Manmade cellulose material obtained by the direct dissolution of cellulose in an organic solvent without the formation of an intermediate compound and subsequent extrusion of the solution of cellulose and organic solvent into a coagulating bath. As used herein, lyocell is distinguished from regenerated cellulose.

Machine direction (MD)—The direction of travel of the forming surface onto which fibers are deposited during formation of a nonwoven web material.

Non-thermoplastic material—Any material which does not fall within the definition of thermoplastic material.

Nonwoven fabric, sheet or web—A material having a structure of individual fibers which are interlaid, but not in an identifiable manner as in a knitted fabric. Nonwoven materials have been formed from many processes such as, for example; meltblowing, spunbonding and water laying processes. The basis weight of nonwoven fabrics is usually expressed in grams per square meter (gsm) and the fiber fineness is measured in denier.

Polymer—Generally includes, for example, homopolymers, copolymers, such as for example, block, graft, random and alternating copolymers, terpolymers, etc, and blends and modifications thereof. Furthermore, unless otherwise specifically limited, the term "polymer" includes all possible geometrical configurations of the material. These configurations include, for example, isotactic, syndiotactic and random symmetries.

Regenerated cellulose—Manmade cellulose obtained by chemical treatment of natural cellulose to form a soluble chemical derivative or intermediate compound and subsequent decomposition of the derivative to regenerate the cellulose. Regenerated cellulose includes spun rayon and regenerated cellulose processes include the viscose process, the cuprammonium process and saponification of cellulose acetate.

Tex—A unit used to indicate the fineness of a filament given by the weight in grams for 1,000 meters of filament. A filament of 1 tex has a mass of 1 gram for 1,000 meters of length.

Thermoplastic material—A polymer that is fusible, softening when exposed to heat and returning generally to its unsoftened state when cooled to room temperature. Thermoplastic materials include, for example, polyvinyl chlorides, some polyesters, polyamides, polyfluorocarbons, polyolefins, some polyurethanes, polystyrenes, polyvinyl alcohol, caprolactams, copolymers of ethylene and at least one vinyl monomer (e.g., poly (ethylene vinyl acetates), and acrylic resins.

SUMMARY OF THE INVENTION

The present invention provides a fibrous nonwoven sheet material that overcomes the above and other related previous problems in the art and yet achieves very good wet strength, excellent hand and aesthetics, high bulk or thickness, uniform liquid release, low linting, good resistance to abrasion and excellent absorption characteristics. The increased strength substantially improves serviceability and resistance to sheet material breaking and tearing during premoistened wipe manufacturing operations, improves handling of the sheet material on automated equipment and allows the finished premoistened wipe to withstand vigorous use.

In addition, the present invention can provide for a wet or dry wipe which has the above advantageous characteristics and which can also, surprisingly, disintegrate or disperse or break up readily in water with mild agitation, such as is present in a standard septic or sanitary system. The inventive sheet material's ability to breakup under mild agitation in water is a function of the sheet material's fiber composition and processing, which allow breakup into individual fibers or small chunks of material. The disintegration is not dependent on wipe size, as are some of the currently available products. Thus, the inventive sheet material affords the opportunity to increase the size of the wiping sheet, making it more useful to the consumer. The inventive nonwoven sheet material is comprised substantially of cellulosic materials so that it is suited for disposal and biodegradation in sanitary systems.

The inventive sheet material does not require special impregnating lotion chemistries to maintain cohesiveness or promote disintegration. The inventive sheet material maintains its wet tensile strength and dispersibility in solutions having a pH in the range of about 3 to about 11. Thus, the inventive sheet material can be impregnated with a wide range of lotion chemistries for use in cleaning and personal care markets, which is very advantageous to wipe manufacturers and end use consumers. Other features and advantages of the present invention will be in part obvious and in part pointed out in more detail hereinafter.

The above and other advantageous results are generally achieved by providing a fibrous, nonwoven sheet material comprising natural cellulose fibers, manmade cellulose fibers and binder. In one aspect of the invention, the sheet material comprises natural cellulose fibers, regenerated cellulose fibers and synthetic binder fibers. In another aspect of the invention, the sheet material comprises wood pulp fibers, lyocell fibers and synthetic binder fibers. In an especially advantageous embodiment, the inventive sheet material comprises about 65 to about 97 percent by weight wood pulp fibers, about 10 to about 30 percent by weight lyocell fibers and about 0.5 to about 3 percent by weight synthetic bicomponent fibers. In some embodiments, the inventive sheet material may incorporate other known papermaking aids and treatments.

The finished sheet material has a basis weight of about 30 to about 90 gsm and a preferred basis weight of about 45 to about 70 gsm. The sheet material will have a preferred wet tensile strength (for a 55 gsm basis weight) of at least about 160 grams per 25 mm in the MD and at least about 100 grams per 25 mm in the CD. The inventive sheet material can advantageously have a "flush break up" (to fibers) of less than about 300 seconds and preferably less than about 200 seconds.

The fibers comprising the inventive nonwoven sheet material can initially be dispersed within a fluid-dispersing medium to form a slurry or furnish. A fibrous, nonwoven web is formed by depositing the slurry on conventional papermaking equipment. After formation and prior to drying, the web material is hydraulically entangled at low energies from one or both sides of the web to form a nonwoven fabric. After entanglement, the fibrous, nonwoven fabric is heated. The heating is carried out under conditions to permit both drying of the fabric and controlled activation of the binder to form an inventive sheet material.

A better understanding of the advantages, features, properties and relationships of the invention will be obtained from the following detailed description, which sets forth-illustrative embodiments and is indicative of the way in which the principles of the invention are employed.

BRIEF DESCRIPTION OF THE DRAWINGS

Other objects and advantages of the invention will be evident to one of ordinary skill in the art from the following detailed description made with reference to the accompanying drawings, in which.

DESCRIPTION OF PREFERRED EMBODIMENT

Figure 1:
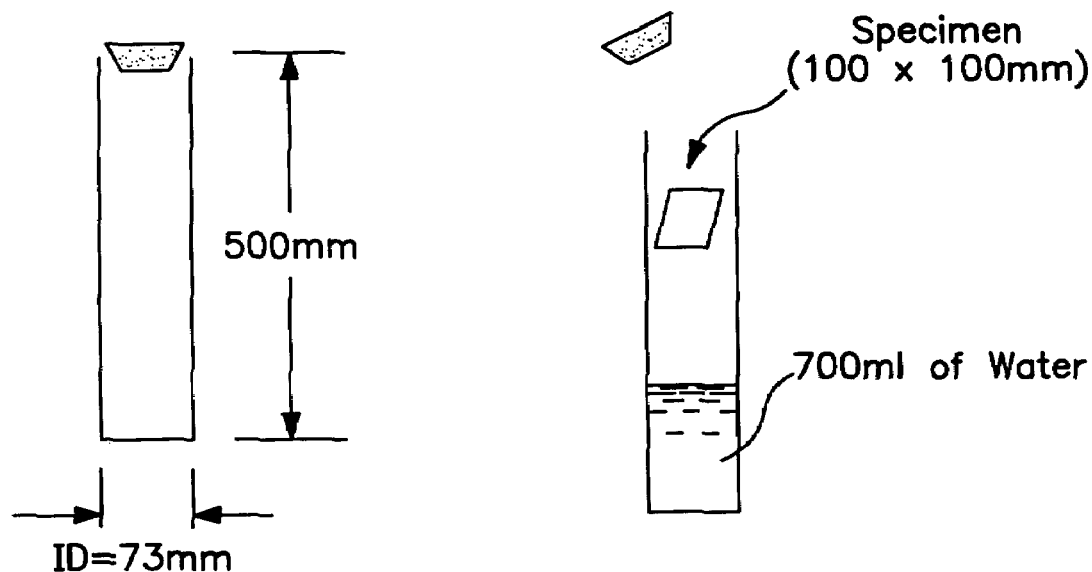
FIG. 1 is a schematic illustration of a Flush Index test.
Figure 1:
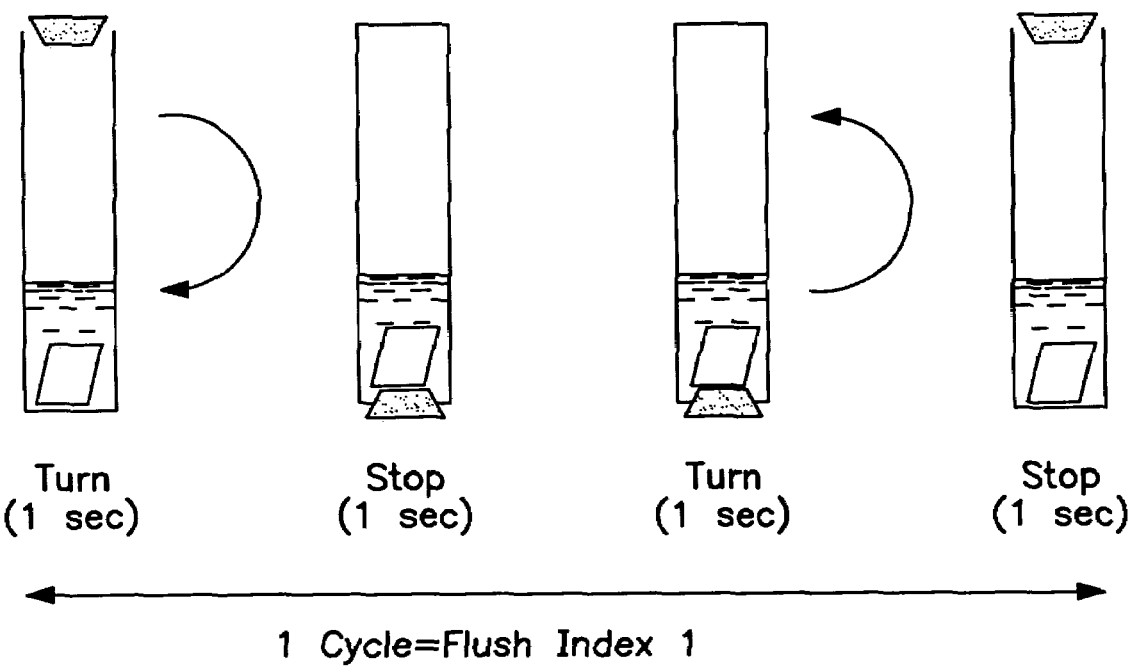

One aspect of the invention comprises a fibrous, nonwoven sheet material comprised substantially of cellulosic materials. The novel materials and construction of the inventive sheet material reduce restrictions as to postformation wipe chemistry. The sheet material has sufficient wet strength for vigorous use as a premoistened wipe. Despite the appreciable wet strength of the inventive sheet material it will, surprisingly, disintegrate or disperse into smaller pieces of sheet material and individual fibers in an relatively short time under mild agitation in water. The substantial cellulosic content of the sheet material provides ready bio-decomposition in most sanitary systems. The inventive sheet material maintains its appreciable wet tensile strength and dispersibility in solutions having a pH in the range of about 3 to about 11.

The inventive sheet material comprises a blend of natural cellulose fibers, manmade cellulose fibers and binder. The natural cellulose component is the major component of the sheet material and is present in a preferred range of about 65 to about 97 percent by weight. This component can be selected from substantially any class of natural cellulose fiber, natural cellulose pulp fiber and blends thereof. Preferably, the pulp fiber is comprised of wood fiber pulp. Other natural cellulose long fiber pulp materials such as, for example, cotton, sisal, hemp, kenaf and blends thereof can also be used in combination with, or in place of, the wood fiber pulp. The selection and processing parameters necessary to achieve desired processed pulp characteristics and web product performance are within the ordinary skill of a practitioner in this art. While it would be possible to replace some or all of the natural cellulose fibers with manmade cellulose fibers, which replacement is encompassed by the present invention, such replacement is not considered economically desirable.

The inventive sheet material also contains about 5 to about 50 percent by weight of manmade cellulose fibers. While the manmade cellulose fibers useful in the invention include regenerated cellulose fibers such as spun rayon, the preferred manmade cellulose fibers include those high crystallinity cellulose fibers having a crystallinity of at least about 40 percent and advantageously at least about 50 percent. The manmade cellulose fibers may consist essentially of high crystallinity cellulose fibers. As used herein, a manmade cellulose fiber consisting essentially of high crystallinity cellulose fibers excludes cellulose fibers have a cellulose crystallinity of less than 40 percent such as spun rayon. The use of the phrase "manmade fibers consisting essentially of high crystallinity cellulose fibers" does not exclude use within the sheet material composition of conventional papermaking aids and treatments as known within the art. Advantageously, the sheet material of the invention comprises about 10 to about 30 percent by weight of high crystallinity cellulose fibers.

Preferably, the high crystallinity cellulose fibers comprise lyocell fibers. As shown below, lyocell fibers possess surprisingly unique and desirable properties when compared to lower crystallinity cellulose fibers such as viscose rayon.

|  | lyocell | modal | viscose rayon |
| --- | --- | --- | --- |
| dtex | 1.7 |  | 1.7 |
| dry tenacity (cN/tex) | 38-42 | 34-36 | 22-26 |
| wet tenacity (cN/tex) | 34-38 | 19-21 | 10-15 |
| initial wet modulus (5%) | 250-270 | 100-120 | 40-50 |
| Total orientation (birefringence) | 0.044 | 0.032 | 0.026 |
| crystallinity (%) | 65 | 45 | 35 |

Interestingly, the inventors have found that there is little difference in the dry strength for nonwoven sheet materials formed using lyocell fibers as compared to similar web materials formed with viscose rayon fibers, even though the dry tenacity of lyocell is substantially higher than that of viscose rayon. Surprisingly however, lyocell fiber containing sheet materials have wet tensile strengths up to about 50 percent higher than similar sheet materials containing viscose rayon. While not wishing to be bound to any theory, the increase in wet tensile strength may be attributable to the highly crystalline and oriented structure of the lyocell fiber.

The lyocell fibers have a preferred length of about 4 to about 12 millimeters (mm) and a preferred fineness of about 1.0 to about 3.0 denier.

The inventive sheet material comprises a minor binder component. Preferably, the binder component comprises synthetic binder fibers. While it is possible to use resin or other non-fiber binders in place of synthetic binder fibers, such use requires a very low amount (typically less than 0.12 by weight) to maintain dispersibility of the resulting sheet material in mildly agitated water, and thus such binder materials are not preferred. As used herein, a synthetic binder fiber includes any polymeric fiber having a thermoplastic portion appropriately positioned and with a melting point low enough to allow some activation and fusing to adjacent sheet material components during heating. Typically, the synthetic binder fibers will comprise at least one polymer having a melting point below about 165° C. Synthetic binder fibers of the invention include, for example, polyolefin fibers, bicomponent fibers and mixtures thereof. The synthetic binder fiber component in the inventive sheet material functions to create a fibrous network that, after activation and fusing, lightly bonds the pulp fibers and high crystallinity cellulose fibers together. This bonded fibrous network of pulp fibers, synthetic binder fibers and high crystallinity cellulose fibers develops a surprising synergy that provides a nonwoven sheet material having greater wet tensile strength than sheet materials comprising pulp fibers, viscose rayon fibers and synthetic fibers, while also functioning to impart desired properties of softness and disintegratibility under mild agitation in water. Preferably, the sheet material of the invention comprises about 0.5 to 3.0 percent by weight of synthetic binder fibers. The presence of the synthetic binder fiber component is required to achieve the preferred high wet tensile strengths disclosed herein. However, it should be noted that the amount of synthetic binder fiber in the finished sheet material should be held to a low amount to assure the ability of the finished sheet material to disintegrate or disperse with mild agitation in water. Naturally, if dispersibility of the nonwoven sheet material in water is not desired, the amount of the synthetic binder fiber component can be increased.

Advantageously, the synthetic binder fibers comprise bicomponent binder fibers having a length of about 6 to about 20 mm and a fineness of about 1.5 to about 9 denier. The bicomponent binder fibers may comprise polymers of, for example, polyethylene (PE), polypropylene (PP), polyethylene terephthalate (PET) and polyester in any combination polyethylene/polypropylene (PE/PP), polyethylene/polyethylene terephthalate (PE/PET), polyethylene terephthalate/polyethylene terephthalate (PET/PET) and polyethylene/polyester are advantageous polymer combinations for bicomponent fibers used in the invention, especially when configured as a higher melting point core and a lower melting point sheath. Preferably, the polymer (or lower melting point polymer for a bicomponent fiber) has a melting point below about 130° C. Celbond T-105, a 12.7 mm by 3 denier PE sheath/polyester core bicomponent fiber available from Kosa of Spartanburg S.C. has been found suitable for use as a synthetic binder fiber in the invention.

In another aspect of the invention fibrous, nonwoven web materials are preferably made using conventional papermaking techniques. In these techniques the fibers are dispersed in a suitable liquid dispersing media to create a furnish. Preferably, water is used as the liquid media in accordance with known papermaking techniques and, accordingly, a furnish comprising water, natural cellulose fibers, manmade cellulose fibers and synthetic binder fibers is formed. The total concentration of fibers in the furnish will be a function of the equipment used and desired equipment processing parameters.

The higher modulus of the lyocell fiber functions to provide a stiffer fiber in the furnish. This characteristic allows the use of lyocell fibers with lengths longer than those typically used with lower modulus manmade cellulose fibers such as spun rayon which tend to have poorer dispersion characteristics in the furnish when used in longer lengths. Use of longer lyocell fibers is believed to contribute to the production of inventive sheet materials having improved wet strength. Surprisingly, the improved wet strength is achieved without significant loss of disintegratibility of the inventive sheet material under mild agitation in water.

As will be appreciated, other known papermaking aids and treatments can be incorporated into the invention. For example, dispersing agents or wet strength agents may be incorporated into the furnish. These materials constitute only a minor portion of the furnish, typically less than one percent by weight, and facilitate uniform fiber deposition while providing the web in its wet condition with sufficient strength so that it will be capable of retaining its integrity during the hydroentangling operation. These dispersants may include natural materials, such as guar gum, karaya gum and the like as well as man-made resin additives.

The furnish is preferably wet laid on a papermaking machine. Although substantially all commercial papermaking machines, including rotary cylinder machines may be used, it is desirable where very dilute fiber furnishes are employed to use an inclined fiber-collecting wire, such as that described in U.S. Pat. No. 2,045,095. The dilute aqueous fiber furnish is fed to a headbox and then to the fiber collecting wire thereof. The fibers are retained on the wire in a random three-dimensional network or configuration with slight orientation in the machine direction while the aqueous dispersant quickly passes through the wire and is rapidly and effectively removed.

The wet laid web material is hydraulically entangled (hydroentangled) to provide the final sheet material with desired cloth-like structure and absorption characteristics, while also increasing the strength of the final sheet material. Advantageously, entanglement is performed prior to a drying operation.

Typically, the hydroentangling operation is carried out in the manner set forth in U.S. Pat. No. 5,009,747 to Viazmensky et al, the disclosure of which is incorporated by reference herein. While the Viazmensky patent relates to a nonwoven web material having a different fiber content, the hydroentangling operation described therein can efficaciously be employed with the web material of the present invention. Thus, as also stated in the aforementioned U.S. Pat. No. 4,755,421, the hydroentanglement treatment entangles together the fibers forming the present web. The synergy between the high crystallinity cellulose fibers and synthetic binder fibers allows the use of lower entanglement energies than for conventional nonwoven materials while yielding both good strength and rapid disintegration in moving water. The entanglement process can be carried out on the forming wire and using total energy input of about 0.005 to 0.035 horsepower-hours per pound of web (Hp-hr/lb).

It should be understood that energy inputs greater than 0.035 Hp-hr/lb can be used in the practice of the invention. However, as the entanglement energy is raised above 0.035 Hp-hr/lb, substrates containing lyocell fibers in excess of 15 percent by weight and with fiber lengths greater than 8 mm can become increasingly difficult to disperse or break up in water. In one embodiment of the invention, the web material is hydroentangled on pattern wires to achieve a disintegratable, nonwoven sheet material having an apertured appearance.

The hydroentangled fabric is dried, for example, over heated drying cans or in an oven to form the final sheet. Advantageously, the drying process is controlled to achieve a desired level of activation and fusion of the synthetic binder fibers. Activation of the synthetic binder fiber lightly bonds the components of the sheet material together to increase tensile strength while still allowing the sheet material to disintegrate under mild agitation in water. Naturally it is also possible to activate the synthetic binder fibers at other stages of sheet material formation. The sheet material is typically not treated with any postformation bonding agent.

The basis weight for the nonwoven sheet material of the present invention is typically in the range of about 30 to about 90 gsm. Advantageously, the inventive nonwoven sheet material exhibits a basis weight of about 45 to about 70 gsm.

The inventive nonwoven sheet material has a preferred wet tensile strength (for a 55 gsm basis weight) of at least about 160 grams per inch MD and at least about 100 grams per inch CD. Naturally, as the basis weight of the sheet material increases the tensile strength of the sheet material will increase.

Wet tensile testing is conducted on a 50 mm wide by 127 mm long sample. The use of a 50 mm wide test sample is found to give much greater precision and repeatability as compared to a 25 mm wide test sample. The sample is soaked in room temperature water. After soaking, the sample is blotted on a cotton blotter to remove excess water. The blotted sample is placed in the jaws of a tensile testing instrument. Suitable tensile testing instruments are available from Instron and Zwick. The tensile testing instrument applies a constant rate of extension of 5 inches per minute until the test sample breaks. A load cell is used to measure the force imposed on the sample at breakage. The force required to break the test sample is divided by two and reported in grams per 25 mm (gm/25 mm).

The ability of a nonwoven sheet material to absorb and hold liquids is an important property for premoistened wipes. Absorption capacity is a measure of the amount of water that the nonwoven sheet material can absorb and hold. To test for absorption capacity, a 3-inch by 3-inch sample is preweighed and saturated by soaking in water for 60 seconds. The saturated sample is suspended by one corner within a 1,500 ml covered beaker containing 200 ml of water. The sample is allowed to hang suspended for 10 minutes. After hanging for 10 minutes the saturated sample is weighed. Percent absorption capacity is calculated using the following formula:

$$(\text{wet weight} - \text{dry weight})/\text{dry weight} \times 100 = \text{Percent Absorption Capacity}$$

Advantageously the inventive nonwoven sheet material of the invention will have an absorption capacity of at least about 400 percent. More advantageously the inventive nonwoven sheet material of the invention will have an absorption capacity in the range of about 500 to about 750 percent.

The ability of a nonwoven web to disperse or disintegrate or break up under mild agitation in water is measured using two different methods, a flush break up test and a Flush Index test. In the Flush Index test or rotating tub test, a 100 mm by 100 mm test sample is placed in a pipe like tub. The pipe is transparent, 500 mm long with an inside diameter of 73 mm. The pipe is closed at one end and contains 700 ml of water. After placing the test sample in the pipe, the open end is capped.

The pipe is rotated end of over end for 180 degrees, held for one second, rotated end over end an additional 180 degrees to arrive at the original starting point and held for one second. Each 180 degree rotation is accomplished in about one second. A complete 360 degree rotation is equal to one cycle or a Flush Index of one. The condition of the specimen is evaluated visually through the pipe walls after each cycle. The test measures the number of 360 degree rotations of the pipe it takes for the test sample to: A) break up into two or more pieces; B) breakup into four to five ⅝ inch pieces; and C) reach a state of substantially individual fibers.

FIG. 1 schematically illustrates the Flush Index test.

The flush break up test measures the time it takes for a test sample of specified size placed in a controlled vortex of water to break up into two or more pieces. In this test 500 ml of tap water is placed into a 600 ml beaker. A magnetic stirring bar with a star shape, a diameter of 35 mm and a height of 12 mm is introduced into the 600 ml beaker. A Nalgene brand star-head stirring bar No. 6600-0035 has been found acceptable. The beaker is placed onto a magnetic stirring plate. The magnetic stirring plate is adjusted so that the bottom tip of the vortex created by the rotation of the stirring bar is approximately one-half inch from the top of the stirring bar. It should be noted that the step of adjusting the vortex is important to reproducibility of the method.

A 50 mm by 50 mm (±1 mm) square sample is placed into the vortex of water in the beaker and a stopwatch is started. The time at which the following events occur is recorded: A) break up into two or more parts; B) breakup into four or five parts; C) equal break up into many (about 10) parts; D) equal break up into more small parts (about 25 or more) than C; E) break up into individual fibers.

U.S. Pat. No. 4,755,421 to Manning et al used a different test to measure break up time of the nonwoven sheet material. Manning tested his sheet material using mild agitation and measuring the time for the sheet material to break up into several ¾ inch pieces. Manning found that substrates having a basis weight of 72.9 gsm and a CD wet tensile strength of 341 grams per 1 inch took 1.5 minutes to break up. A sheet material of the present invention having a 70 gsm basis weight and a CD wet tensile strength of 445 grams per 25 mm, when placed under the test conditions of Manning, broke up into several ¾ inch pieces in 1.4 minutes and broke up into about 25 pieces in 1.9 minutes. Thus, the nonwoven sheet material of the present invention provides an improvement over the material of the Manning reference.

The following examples are given for purposes of illustration only in order that the present invention may be more fully understood. These examples are not intended to limit in any way the practice of the invention. Unless otherwise specified, all parts are given by weight.

EXAMPLE 1

A series of nonwoven sheet samples were produced. The samples were formed on an inclined wire papermaking machine set at 75 feet per minute and a basis weight of 55 gsm. The wet web materials were passed under two water jet entanglement nozzles, each nozzle fitted with a strip having 51 holes per inch, each hole having an orifice diameter of 92 microns. The nozzle pressures were set at 400 and 450 psi, yielding entanglement energy of 0.028 Hp-hr/lb. The web materials were supported on a forming fabric during the entanglement phase of production. The web materials were then dried on steam heated rotary drying cans having a temperature of about 300 degrees Fahrenheit. Synthetic binder fibers were activated during drying.

Each of the samples comprised the same type and percentage of wood pulp fibers and bicomponent binder fibers. Additionally, sample 1a comprised 20 percent, 8 mm by 1.5 denier viscose rayon fiber. Sample 1b replaced the viscose rayon fiber with 20 percent, 8 mm by 1.5 denier lyocell fiber. Sample 1c replaced the viscose rayon fiber with 20 percent, 10 mm by 1.5 denier lyocell fiber.

TABLE 1

| Sample | 1a | 1b | 1c |
|---|---|---|---|
| % Wood Pulp | 78.5 | 78.5 | 78.5 |
| % Bicomponent | 1.5 | 1.5 | 1.5 |
| % Viscose Rayon | 20 | — | — |
| % Lyocell (8 mm × 1.5 dpf) | — | 20 | — |
| % Lyocell (10 mm × 1.5 dpf) | — | — | 20 |
| Entanglement energy (Hp-hr/lb) | 0.028 | 0.028 | 0.028 |
| Basis Weight (gsm) | 54.9 | 54.5 | 55.6 |
| Thickness (microns) | 440 | 445 | 491 |
| Wet Tensile (gm/25 mm) | | | |
| MD | 160 | 235 | 275 |
| CD | 138 | 188 | 225 |
| Average | 150 | 212 | 250 |
| Flush Index (rotations to state C) | 21 | 19 | 16 |
| Flush Break Up (sec) | | | |
| B | 29 | 35 | 37 |
| D | 43 | 60 | 59 |
| E | 162 | 203 | 165 |

As can be seen from TABLE 1, samples 1b and 1c have substantially improved wet tensile strength over sample 1a, while also providing surprisingly better disintegratibility as shown by the Flush Index test results. The longer lyocell fibers used in sample 1c provide that sample with increased wet tensile strength as compared to sample 1b which uses shorter lyocell fibers.

EXAMPLE 2

Samples of a disintegratable nonwoven sheet were produced on an inclined wire paper making machine set at a speed of 130 meters per minute and a basis weight of 55 gsm. Sample 2a was comprised of wood pulp fibers, bicomponent binder fibers and 8 mm by 1.5 denier viscose rayon fibers. Sample 2b was comprised of wood pulp fibers, bicomponent binder fibers and 10 mm by 1.25 denier lyocell fibers. Each web material was passed under three water jet entanglement nozzles, each nozzle fitted with a strip having 51 holes per inch, each hole having an orifice diameter of 92 microns. The pressure on the three rows of nozzles was set at 440 psi each, yielding a total entanglement energy of 0.007 Hp-hr/lb. The web materials were supported on a fabric during the entanglement phase of production. The fabrics were then dried on rotary drying cans heated to about 300 degrees Fahrenheit and through air dryers set at a temperature of about 390 degrees Fahrenheit. Synthetic binder fibers were activated during drying.

TABLE 2

| Sample | 2a | 2b |
|---|---|---|
| % Wood Pulp | 78.5 | 79 |
| % Bicomponent | 1.5 | 1.0 |
| % Viscose Rayon (8 mm × 1.5 dpf) | 20 | — |
| % Lyocell (10 mm × 1.25 dpf) | — | 20 |
| Entanglement energy (Hp-hr/lb) | 0.008 | 0.008 |
| Basis Weight (gsm) | 56.0 | 55.3 |
| Thickness (microns) | 564 | 558 |
| Wet Tensile (gm/25 mm) | | |
| MD | 235 | 360 |
| CD | 143 | 240 |
| Average | 189 | 300 |
| Flush Break Up (sec) | | |
| B | 33 | 34 |
| D | 67 | 52 |
| E | 216 | 150 |

Sample 2a comprises higher binder fiber concentrations than sample 2b. Despite a lower binder fiber concentration, sample 2b has substantially improved wet tensile strength over the sheet material of sample 2a, while also surprisingly providing better disintegratibility as shown by the Flush Break Up test results.

EXAMPLE 3

A series of nonwoven sheets were produced on an inclined wire papermaking machine set at 75 feet per minute and a basis weight of 55 gsm. The wet web materials were passed under two water jet entanglement nozzles; each nozzle fitted with a strip having 51 holes per inch, each hole having an orifice diameter of 92 microns. The nozzle pressures were set at 365 and 445 psi yielding 0.026 Hp-hr/lb entanglement energy. The substrates were supported on a forming fabric during the entanglement phase of production. The fabrics were then dried on steam heated rotary drying cans having a temperature of about 300 degrees Fahrenheit. Synthetic binder fibers, if present, were activated during the drying step.

TABLE 3

| Sample | 3a | 3b | 3c | 3d |
|---|---|---|---|---|
| % Wood Pulp | 80 | 80 | 78.5 | 78.5 |
| % Bicomponent | 0 | 0 | 1.5 | 1.5 |
| % Viscose Rayon (8 mm × 1.5 dpf) | 20 | — | 20 | — |
| % Lyocell (8 mm × 1.5 dpf) | — | 20 | — | 20 |
| Entanglement energy (Hp-hr/lb) | 0.026 | 0.026 | 0.026 | 0.026 |
| Basis Weight (gsm) | 53.0 | 52.0 | 55 | 55.6 |
| Thickness (microns) | 469 | 435 | 445 | 430 |
| Wet Tensile (gm/25 mm) | | | | |
| MD | 113 | 150 | 190 | 280 |
| CD | 105 | 130 | 155 | 225 |
| Average | 109 | 140 | 173 | 252 |
| Flush Break Up (sec) | | | | |
| B | 15 | 15 | 26 | 37 |
| D | 31 | 31 | 47 | 59 |
| E | 150 | 150 | 99 | 165 |

As can be seen from TABLE 3, presence and activation of synthetic binder fibers in the sheet material provides large increases in wet tensile strength. Use of high crystallinity manmade cellulose fibers in the absence of a synthetic fiber binder (sample 3b) provides only a small wet tensile strength advantage over a similar material incorporating rayon fibers in place of the high crystallinity cellulose fibers (sample 3a). While use of a synthetic binder fiber increases the wet tensile strength of the rayon containing sheet material (sample 3c) and the lyocell containing sheet material (sample 3d), the wet tensile strength of the high crystallinity cellulose fiber sheet material is increased to a surprisingly greater degree.

EXAMPLE 4

An aqueous furnish comprising (dry weight) 45 percent Irving northern softwood kraft fibers, 37 percent Brunswick southern softwood kraft fibers, and 18 percent, 8 mm by 1.5 denier viscose rayon fibers was prepared. The furnish was made without binder fibers and contained no wet strength agent. The furnish was fed to an inclined wire papermaking machine set at 75 feet per minute and a basis weight of 55 gsm. The web material was passed under two water jet entanglement nozzles, each nozzle fitted with a strip having 51 holes per inch, each hole having an orifice diameter of 92 microns. The nozzle pressures were varied to achieve different levels of entanglement energy on the samples. The web material was supported on a forming fabric during the entanglement phase of production. The fabrics were then dried on steam heated rotary drying cans having a temperature of about 300 degrees Fahrenheit.

TABLE 4

| Sample | Entanglement energy (HP-hr/lb) | CD Wet Tensile (gm/25 mm) | Flush Index (rotations to state C) |
|---|---|---|---|
| 4a | 0.0 | 79 | 3.5 |
| 4b | 0.008 | 71 | 5.0 |
| 4c | 0.013 | 61 | 7.5 |
| 4d | 0.025 | 89 | 11 |
| 4e | 0.049 | 114 | 18 |
| 4f | 0.07 | 144 | 23 |

Figure 2:
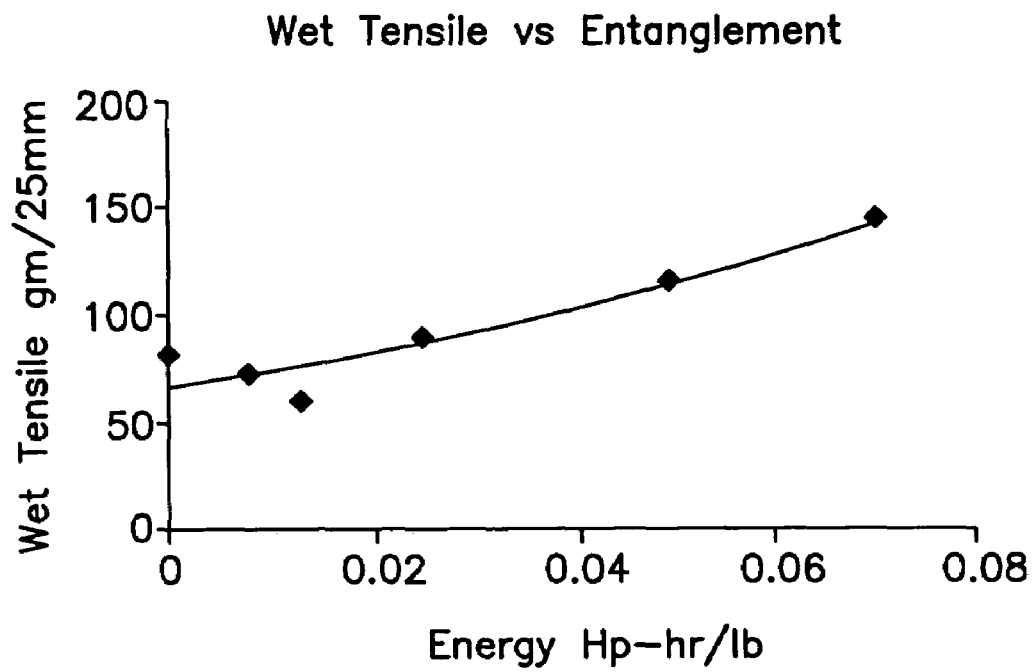
FIG. 2 is a graph of wet tensile strength versus hydroentanglement energy.
Figure 3:
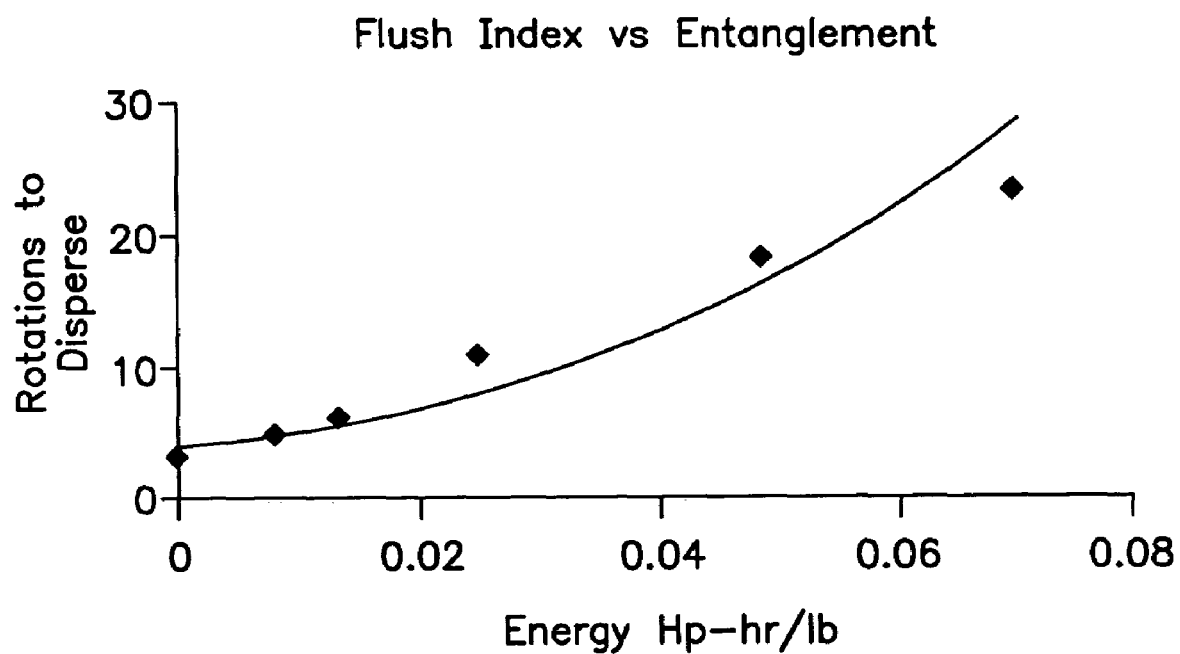
FIG. 3 is a graph of Flush Index versus hydroentanglement energy.

The results of Table 4 are shown graphically in FIGS. 2 and 3.

EXAMPLE 5

An aqueous furnish comprising (by dry weight) 52 percent Irving northern softwood kraft, 26 percent Brunswick southern softwood kraft fibers, 20 percent, 10 mm by 1.25 denier lyocell fiber and 1.5 percent Celbond T-105, 0.5 inch by 3 denier bicomponent binder fibers was prepared. The furnish contained no wet strength agents. The sheet was formed on an inclined wire papermaking machine set at 75 feet per minute and a basis weight 55 gsm. The wet web materials were passed under two water jet entanglement nozzles, each nozzle fitted with a strip having 51 holes per inch, each hole having an orifice diameter of 92 microns. The nozzle pressures were varied to achieve a constant level of entanglement energy, (about 0.022 Hp-hr/lb) as the basis weight of the sheet was varied. The web materials were supported on a forming fabric during the entanglement phase of production. The web materials were dried on steam heated rotary drying cans having a temperature of about 300 degrees Fahrenheit. Binder fibers were activated during drying.

TABLE 5

| Sample | 5a | 5b | 5c | 5d | 5e | 5f |
|---|---|---|---|---|---|---|
| Basis Weight (gsm) | 40 | 45 | 55 | 70 | 80 | 100 |
| Entanglement Energy (Hp-hr/lb) | 0.023 | 0.023 | 0.021 | 0.022 | 0.022 | 0.022 |
| Thickness (microns) | 498 | 527 | 549 | 626 | 661 | 726 |
| Wet Tensile (gm/25 mm) | | | | | | |
| MD | 140 | 204 | 360 | 508 | 837 | 1255 |
| CD | 150 | 263 | 262 | 445 | 640 | 628 |
| Average | 145 | 234 | 311 | 477 | 739 | 942 |
| Flush Break Up (sec) | | | | | | |
| B | 71 | 48 | 60 | 84 | >400 | >400 |
| D | 81 | 89 | 92 | 116 | | |
| E | 116 | 95 | 139 | 272 | | |

As shown in TABLE 5, the wet tensile strength increases with increasing basis weight and the disintegratibility under mild agitation in water decreases with increasing basis weight.

EXAMPLE 6

A furnish comprising (by dry weight) 52 percent Irving northern softwood kraft fibers, 26 percent Brunswick southern softwood kraft fibers, 20 percent, 10 mm by 1.25 denier lyocell fiber and 1.5 percent Celbond T-105, 0.5 inch by 3 denier bicomponent binder fibers was prepared. The furnish contained no wet strength agents. The sheet was formed on an inclined wire papermaking machine set at 75 feet per minute and a basis weight 55 gsm. The wet web materials were passed under two water jet entanglement nozzles, each nozzle fitted with a strip having 51 holes per inch, each hole having an orifice diameter of 92 microns. The nozzle pressures were varied to achieve a constant level of entanglement energy, (about 0.035 Hp-hr/lb), as the basis weight of the sheet was varied. The web materials were supported on a forming fabric during the entanglement phase of production. The web materials were dried on steam heated rotary drying cans having a temperature of about 300 degrees Fahrenheit. Binder fibers were activated during drying.

TABLE 6

| Sample | 6a | 6b | 6c | 6d | 6e | 6f |
|---|---|---|---|---|---|---|
| Basis Weight (gsm) | 40 | 45 | 55 | 70 | 85 | 100 |
| Entanglement Energy (Hp-hr/lb) | 0.033 | 0.035 | 0.036 | 0.034 | 0.031 | 0.036 |
| Thickness (microns) | 429 | 463 | 527 | 610 | 680 | 741 |
| Wet Tensile (gm/25 mm) | | | | | | |
| MD | 125 | 244 | 469 | 900 | 1403 | 2000 |
| CD | 120 | 210 | 394 | 708 | 1125 | 1325 |
| Average | 123 | 227 | 432 | 804 | 1264 | 1663 |
| B | >400 | >400 | >400 | >400 | >400 | >400 |

As shown in TABLE 6, the wet tensile strength increases with increasing basis weight and the disintegratibility under mild agitation in water decreases with increasing basis weight.

EXAMPLE 7

A series of furnishes comprising 8 mm by 1.5 denier viscose rayon fibers, Irving northern softwood kraft pulp fibers and Celbond T-105 bicomponent binder fibers were prepared. The amounts of bicomponent fibers and wood pulp fibers were changed to study the effect of the changing concentrations on wet tensile strength and disintegration characteristics of the resulting sheet. The sheet was formed on an inclined wire papermaking machine set at 75 feet per minute and a basis weight 55 gsm. The wet web materials were passed under two water jet entanglement nozzles, each nozzle fitted with a strip having 51 holes per inch, each hole having an orifice diameter of 92 microns. The nozzle pressures were set to achieve an entanglement energy of about 0.025 Hp-hr/lb. The web materials were supported on a forming fabric during the entanglement phase of production. The web materials were dried on steam heated rotary drying cans having a maximum temperature of about 300 degrees Fahrenheit. Binder fibers were activated during drying.

TABLE 7

| Sample | 7a | 7b | 7c | 7d |
|---|---|---|---|---|
| % Wood Pulp | 80 | 79 | 78.5 | 78 |
| % Bicomponent | 0.0 | 1.0 | 1.5 | 2.0 |
| % Rayon | 20 | 20 | 20 | 20 |
| Wet Tensile (gm/25 mm) | | | | |
| MD | 160 | 154 | 160 | 198 |
| CD | 97 | 140 | 138 | 172 |
| Average | 147 | 147 | 147 | 147 |
| Flush Index (C) | 4 | 17 | 21 | 31 |

As will be appreciated to persons skilled in the art, various modifications, adaptations, and variations of the foregoing specific disclosure can be made without departing from the teachings of the present invention.

What is claimed is:

1. A fibrous nonwoven web material comprising at least about 50 percent by weight natural cellulose fibers, at least about 5 percent by weight manmade high crystallinity cellulose fibers having a crystallinity of at least about 40 percent and a binder component comprising 0.5 percent to less than 2 percent by weight of binder fibers; wherein the web material is entangled, has a dried basis weight in the range of about 30 to about 90 grams per square meter, has a wet tensile strength (for a 55 gsm basis weight) in the machine direction of at least about 160 gms/25 mm, and has a maximum flush break up time (B) of 45 seconds, and wherein the binder fibers consist of bicomponent fibers, each of the bicomponent fibers having a sheath consisting of at least one of polyethylene and polypropylene.

2. The web material of claim 1, comprising about 65 percent to about 97 percent by weight natural cellulose fibers, and about 10 percent to about 30 percent by weight high crystallinity cellulose fibers.

3. The web material of claim 1, wherein a portion of the binder fibers are activated to increase the tensile strength of the web material as compared to the web material prior to activation.

4. The web material of claim 1, having a wet tensile strength at least about 20 percent greater than the wet tensile strength of a similar web material using regenerated cellulose fibers in place of the high crystallinity cellulose fibers.

5. The web material of claim 1, wherein the high crystallinity cellulose fibers have a crystallinity of at least about 50 percent.

6. The web material of claim 1, formed by wet laying the natural cellulose fibers, the high crystallinity cellulose fibers and the binder fiber from an aqueous mixture.

7. The web material of claim 1, wherein the high crystallinity cellulose fibers have a crystallinity of at least about 58 percent, a dry tenacity of at least about 30 cN/tex and a initial wet modulus of at least about 90 (5 percent).

8. The web material of claim 1, wherein the sheet material will disperse into pieces under mild agitation in an aqueous environment having a pH in the range of about 4 to about 10.

9. A method for making a nonwoven fibrous sheet comprising:
dispersing a major amount of natural cellulose fibers, a lesser amount of manmade high crystallinity cellulose fibers having a crystallinity of at least about 40 percent and a binder component comprising 0.5 percent to less than 2 percent by weight of synthetic binder fibers in a liquid dispersing media to form a furnish, the binder fibers consisting of bicomponent fibers, each of the bicomponent fibers having a sheath consisting of at least one of polyethylene and polypropylene;
wet laying the furnish over a foraminous member to form a nonwoven web;
hydroentangling the nonwoven web; and
heating and drying the hydroentangled nonwoven web to form the sheet,
wherein the sheet has a Flush Index to a state of substantially individual fibers of less than about 20 rotations and the sheet has a machine direction wet tensile strength (for a 55 gsm basis weight) of at least about 160 grams/ 25 mm.

10. The method of claim 9, comprising activating a portion of the synthetic binder fibers, wherein most of the synthetic binder fibers in the sheet are at least partially bonded to some of the natural cellulose fibers and high crystallinity cellulose fibers.

11. The method of claim 9, wherein the step of hydroentangling comprises hydroentangling at a total energy input in the range of about 0.005 to about 0.035 horsepower-hours per pound of nonwoven web.

12. The method of claim 9, wherein the sheet has a machine direction wet tensile strength (for a 55 gsm basis weight) of at least about 200 grams/25 mm.

13. A nonwoven sheet material, wet laid from an aqueous mixture and subsequently hydroentangled, the sheet material comprising about 50 percent to about 97 percent by weight natural cellulose pulp fibers, about 5 percent to about 40 percent by weight manmade cellulose fibers having a crystallinity of at least about 40 percent and a binder component consisting of 0.5 percent to less than 2 percent by weight of synthetic binder fibers and optionally 0.1 percent by weight to 2.0 percent by weight of a non-fiber binder, wherein the binder fibers consist of bicomponent fibers, each of the bicomponent fibers having a sheath consisting of at least one of polyethylene and polypropylene, and a portion of the binder fibers in the sheet material is at least partially bonded to some of the natural cellulose pulp fibers and manmade cellulose fibers so that the sheet material is suitable for use as a premoistened wipe and has a flush break up time to fibers of less than 300 seconds.

14. The sheet material of claim 13, wherein the manmade cellulose fibers have a crystallinity of at least 58 percent, a wet tenacity of at least 30 cN/tex and an initial wet modulus (5 percent) of at least 200.

15. The sheet material of claim 13, wherein the manmade cellulose fibers are selected from lyocell, modal rayon and spun rayon.

16. A premoistened wipe, comprising a nonwoven, hydroentangled sheet material comprised of about 50 percent to about 97 percent by weight natural cellulose pulp fibers, about 5 percent to about 40 percent by weight manmade cellulose fibers having a crystallinity of at least about 40 percent and a binder component comprising 0.5 percent to less than 2 percent by weight of synthetic binder fibers, wherein the binder fibers consist of bicomponent fibers, each of the bicomponent fibers having a sheath consisting of at least one of polyethylene and polypropylene, a portion of the binder fibers in the sheet material is at least partially bonded to some of the natural cellulose pulp fibers and manmade cellulose fibers and the wipe has a maximum flush break up time (B) of 45 seconds in water at most pH ranges.

17. The wipe of claim 16, wherein the manmade cellulose fibers have a crystallinity of at least about 45 percent.

18. The wipe of claim 16, wherein the nonwoven sheet material is impregnated with a chemical solution having a pH in the range of about 3 to about 11.

19. The wipe of claim 16 wherein the nonwoven, hydroentangled sheet material has a machine direction wet tensile strength (for a 55 gsm basis weight) of at least about 100 grams/25 mm.

20. The nonwoven web material of claim 1 wherein the binder fibers comprise at least one polymer having a melting point below 165° C.

21. The nonwoven web material of claim 1 wherein the binder fibers comprise at least one polymer having a melting point below 165° C.

* * * * *